United States Patent
Iizuka et al.

(10) Patent No.: US 6,896,035 B2
(45) Date of Patent: May 24, 2005

(54) MANUFACTURING METHOD FOR CONTINUOUSLY CAST PRODUCT OF STEEL

(75) Inventors: Yukinori Iizuka, Tokyo (JP); Yutaka Awajiya, Fukuyama (JP); Masayuki Nakada, Fukuyama (JP); Makoto Suzuki, Fukuyama (JP); Koichi Tsutsumi, Fukuyama (JP)

(73) Assignee: NKK Corporation, Tokyo (JP)

( * ) Notice: Subject to any disclaimer, the term of this patent is extended or adjusted under 35 U.S.C. 154(b) by 0 days.

(21) Appl. No.: 10/322,943

(22) Filed: Dec. 18, 2002

(65) Prior Publication Data

US 2003/0141036 A1 Jul. 31, 2003

Related U.S. Application Data

(63) Continuation of application No. PCT/JP01/10428, filed on Nov. 29, 2001.

(30) Foreign Application Priority Data

Apr. 25, 2001 (JP) .......................................... 2001-127369
Sep. 26, 2001 (JP) .......................................... 2001-294017

(51) Int. Cl.⁷ .......................... B22D 11/16; B22D 11/20; B22D 11/22
(52) U.S. Cl. ...................... 164/454; 164/455; 164/413; 164/414
(58) Field of Search ................................. 164/476, 477, 164/452, 454, 455, 413, 414, 150.1, 151.2, 154.1, 154.2

(56) References Cited

U.S. PATENT DOCUMENTS 3,543,567 A * 12/1970 Kurz et al. ................... 73/627

FOREIGN PATENT DOCUMENTS

| JP | 52-130422 A | 11/1977 | | |
|---|---|---|---|---|
| JP | 52-130422 | * 11/1977 | .......... | B22D/11/12 |
| JP | 53-057088 A | 5/1978 | | |
| JP | 53-106085 A | 9/1978 | | |
| JP | 53-106085 | * 9/1978 | .......... | G01N/29/04 |
| JP | 57-73670 A | 5/1982 | | |
| JP | 57-106855 | * 7/1982 | .......... | G01N/29/04 |
| JP | 60-100758 A | 6/1985 | | |
| JP | 61-37356 A | 2/1986 | | |
| JP | 62-148850 | * 7/1987 | .......... | G01N/29/00 |
| JP | 62-148850 A | 7/1987 | | |
| JP | 9-174213 A | 7/1997 | | |
| JP | 10-197502 A | 7/1998 | | |
| JP | 11-183449 A | 7/1999 | | |
| JP | 2000-266730 A | 9/2000 | | |

OTHER PUBLICATIONS

European Search Report for European Application No. EP 01274217.
Patent Abstracts of Japan, vol. 011, No. 378 (P–645), abstract of JP Publication No. 62 148851 A published Jul. 2, 1987.
Patent Abstracts of Japan, vol. 1998, No. 12, abstract of JP Publication No. 10 197502 A published Jul. 31, 1998.

* cited by examiner

Primary Examiner—Kevin P. Kerns
(74) Attorney, Agent, or Firm—Frishauf, Holtz, Goodman & Chick, P.C.

(57) ABSTRACT

A manufacturing method for a continuously cast product of steel includes the steps of detecting a position of crater end of product by a method for measuring a solidification state of continuously cast product using a sensor arranged so as to be in non-contact with the product, and controlling at least one condition selected from the conditions of the casting speed and the quantity of secondary cooling water based on the detected position of crater end. The method for measuring a solidification state of continuously cast product includes the steps of cooling the product until a surface layer portion thereof is α transformed, transmitting transverse waves of electromagnetic ultrasonic waves to the cooled product, receiving the signal after the transmitting signal propagates in the product, and judging the solidification state of the product based on the received signal.

9 Claims, 7 Drawing Sheets

MANUFACTURING METHOD FOR CONTINUOUSLY CAST PRODUCT OF STEEL

This application is a continuation application of International Application PCT/JP01/10428 (not published in English) filed Nov. 29, 2001.

BACKGROUND OF THE INVENTION

1. Field of the Invention

The present invention relates to a manufacturing method for a continuously cast product of steel and, more particularly, to a method for controlling casting conditions by detecting the position of a solidification end (referred to as a crater end) of a cast product.

2. Description of Related Arts

In continuous casting of steel, in order to improve the productivity and quality of product, it is very important that the position of a crater end of cast product in the casting direction be detected, and casting conditions be controlled based on the detection result.

For example, if the casting speed is increased to improve the productivity, the crater end moves to the downstream side in the casting direction. However, if the crater end moves beyond a region in which product support rolls lie, the product is swelled by static pressure (referred to as bulging), which presents a problem of degraded quality or casting stop due to large bulging. Also, in the case where soft reduction is applied to a product to decrease central segregation of product and thereby achieve high quality, it is necessary to control the casting speed and the quantity of secondary cooling water so that the crater end is positioned in a soft reduction zone. Further, in the case where the position of crater end is varied greatly in the casting direction by the change of casting conditions, a product on the upstream side of crater end in the casting direction solidifies first, and the supply of molten steel to the downstream side is stopped, so that porosity or laminar voids are created in the central portion of product, which causes a defect that greatly decreases the yield of final product. Also, in the case where the position of crater end varies greatly in the casting direction, even if the casting speed and the quantity of secondary cooling water are controlled, it is difficult to induce the crater end to the soft reduction zone.

In order to detect the position of crater end, it is necessary to continuously measure the solidification state of product. Various methods for this measurement have been proposed so far. Among these methods, many methods in which the transverse waves of ultrasonic waves (hereinafter referred to as transverse ultrasonic waves) are utilized have been proposed. This is because since the transverse ultrasonic wave has a property such that it propagates in a solid phase only and does not propagate in a liquid phase, if the transverse ultrasonic waves are transmitted in the thickness direction at a position of product and a signal indicating that the transverse ultrasonic waves have propagated in the product is detected, it can be judged that the position has been solidified completely, and if the signal is not obtained, it can be judged that unsolidified layer remains. Also, there is available a method in which the position of crater end is estimated from time of flight in which the transverse ultrasonic waves propagates in a product.

As a method for generating the transverse ultrasonic waves in a hot product and detecting them, an electromagnetic ultrasonic wave method in which ultrasonic waves are transmitted and received electromagnetically is known. As a method for measuring the solidification state of product by using the electromagnetic ultrasonic wave method, a method in which a product is held between two transverse ultrasonic wave sensors and the signal intensity of transverse ultrasonic waves having propagated in the product is measured has been disclosed in JP-A-52-130422.

JP-A-62-148850 discloses a method in which an electromagnetic ultrasonic wave sensor capable of generating longitudinal waves and transverse waves at the same time is used to measure the solidification state by the signal intensity of transverse ultrasonic waves, and the variations in liftoff (gap between product and sensor) and the abnormality of sensor are checked at the same time by additionally using a signal of longitudinal ultrasonic waves propagating in an unsolidified layer.

JP-A-10-197502 discloses a method in which a resonance frequency of transverse ultrasonic waves in a product is measured, and a solid phase ratio (ratio of solid phase to solid-liquid coexistence phase) is determined from this resonance frequency.

However, in these methods for measuring the solidification state of product by using electromagnetic ultrasonic waves, the sensitivity is low and the S/N (signal-to-noise ratio) is also low, so that sufficient measurement accuracy cannot be obtained. Also, for this reason, the liftoff of electromagnetic ultrasonic wave sensor is inevitably decreased to about 2 mm, so that continuous measurement cannot be made stably for a long time.

To solve the problem, for example, JP-A-11-183449 discloses a method in which a touch roll is installed on the sensor and the touch roll is pushed against a product to make continuous measurement for a long time. In this method, however, if the sensor is used continuously in an environment in which the temperature exceeds several hundred degrees Centigrade and much scale exists, the scale gets stuck between the sensor and the product, so that the sensor may be damaged or the touch roll sticks to the product, which makes continuous measurement difficult.

Therefore, it is necessary that the liftoff be widened by increasing the sensitivity of electromagnetic ultrasonic wave sensor and that the measurement be done in a non-contact manner without the use of touch roll.

As a method for increasing the sensitivity of electromagnetic ultrasonic wave sensor, JP-A-53-106085 discloses a method in which electromagnetic ultrasonic waves by Lorentz's force is used and a cooling fluid is blown to a hot steel to decrease the temperature of steel to a temperature not higher than the Curie point, by which the steel is magnetized and the electric conductivity is increased. In this method, since the driving force F of electromagnetic ultrasonic waves by Lorentz's force is expressed by F=B×J by using magnetic flux density B and electric current density J, as B and J increase, the sensitivity is made higher.

JP-A-2000-266730 discloses a method in which a burst-like transmitting signal in which at least one selected from frequency, amplitude, and phase is modulated within a predetermined pulse width is used, and correlation operation of receiving signal is performed by using a reference signal of a waveform that is the same as or similar to the transmitting signal. In this method, the correlation between receiving signal and transmitting signal is high, and the correlation between noise and transmitting signal is low, so that the S/N is increased by the correlation operation.

JP-A-53-57088 discloses a method in which receiving signals are averaged in synchronization with an electromagnetic ultrasonic wave generator. In this method, noise has a random waveform generated for each pulse repetition, so that the S/N is increased by averaging.

However, in the method described in JP-A-53-106085, the magnetic flux density of steel is low near the Curie point, so that the steel must be cooled rapidly to a temperature range 200° C. or more lower than the Curie point to obtain a high magnetic flux density, which impairs the quality of product. Also, the conversion efficiency of electromagnetic ultrasonic waves by Lorentz's force is very low essentially, so that an effect of increasing the S/N is little.

If electromagnetic ultrasonic waves are applied to the method described in JP-A-2000-266730, since the receiving signal is far weaker than the transmitting signal and the transmitting signal leaks into the receiving signal, if the pulse width of burst wave is too long, the transmitting signal hides the receiving signal. In particular, if this method is applied to continuous casting, the inside temperature of product changes during the operation, and the position at which the receiving signal appears varies, so that the pulse width cannot be made too long, and an effect of increasing the S/N is little.

If the method described in JP-A-53-57088 is applied to continuous casting, the position at which the receiving signal appears varies as described above, so that the average number must be increased. Therefore, an effect of increasing the S/N is little.

As described above, in the prior art, since the S/N cannot be increased sufficiently, the liftoff of electromagnetic ultrasonic wave sensor cannot be increased, so that the position of crater end cannot be detected stably and exactly in a non-contact state.

SUMMARY OF THE INVENTION

An object of the present invention is to provide a manufacturing method for a continuously cast product, in which the position of a crater end is detected stably and exactly in a state of non-contact with the product, and hence a high-quality product can be manufactured without a decrease in productivity.

The above object is attained by a manufacturing method for a continuously cast product of steel comprising the steps of: detecting a position of crater end of product by using a method (1) for measuring a solidification state of continuously cast product by a sensor arranged so as to be in non-contact with the product; and controlling at least one condition selected from the conditions of the casting speed and the quantity of secondary cooling water based on the detected position of crater end, the method (1) for measuring a solidification state of continuously cast product comprising the steps of: cooling the product until a surface layer portion thereof is α transformed; transmitting transverse waves of electromagnetic ultrasonic waves to the cooled product as a transmitting signal; receiving a signal after the transmitting signal penetrates the product as a receiving signal; and judging the solidification state of the product based on the receiving signal.

As the above-described method for measuring a solidification state of continuously cast product by the sensor arranged so as to be in non-contact with the product, the following two methods can be applied in addition to the above-described method (1).

(2) A method comprising the steps of: transmitting transverse waves of burst-like electromagnetic ultrasonic waves, in which at least one selected from frequency, amplitude, and phase is modulated within a pulse width that has a magnitude of 50 to 150% of the maximum time width not exceeding a time of flight time for propagating in the product, to the product as a transmitting signal; receiving a signal after the transmitting signal propagates in the product as a receiving signal; and judging the solidification state of the product by performing correlation operation of the receiving signal by using a reference signal of a waveform that is the same as or similar to the transmitting signal.

(3) A method comprising the steps of: transmitting transverse waves of electromagnetic ultrasonic waves to the product repeatedly in pulse units as a transmitting signal; receiving a signal after the transmitting signal propagates in the product as a receiving signal; and judging the solidification state of the product by averaging pulses and performing signal processing of receiving signal so that the average number is not less than 16 times and not more than pulse cycles in which signal intensity after the averaging does not decrease.

DETAILED DESCRIPTION OF THE INVENTION

The inventors conducted studies on the sensitivity of a sensor at the time when an electromagnetic ultrasonic wave sensor is arranged so as not to be in contact with a product being continuously cast and the transverse waves of electromagnetic ultrasonic waves are transmitted and received. As a result, the inventors found that a high S/N can be obtained by three methods described below.

(1) First Method

A first method is one in which a product is cooled until the surface layer portion is α transformed, the transverse waves of electromagnetic ultrasonic waves are transmitted as a transmitting signal to a portion α transformed by cooling by a transmitting sensor, and a signal after the transmitting signal propagates in the product is received as a receiving signal by a receiving sensor.

Figure 1:
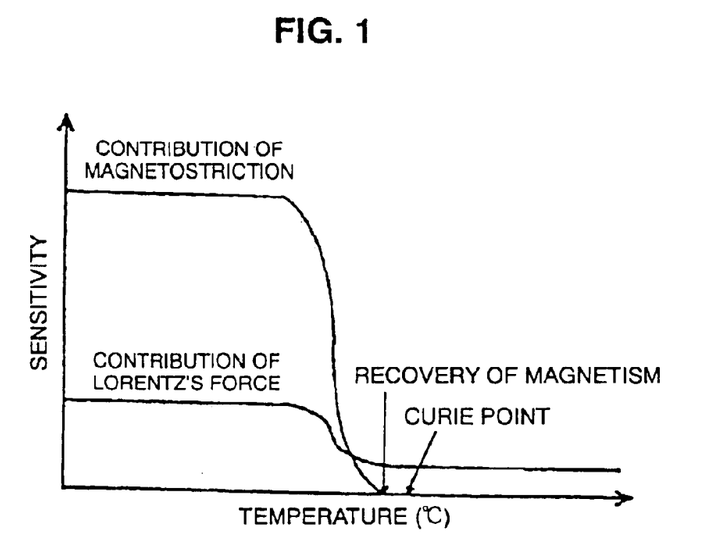
FIG. 1 is a diagram schematically showing the relationship between temperature of steel and sensitivity of electromagnetic ultrasonic wave sensor.

The first method differs from the method described in JP-A-53-106085 in that the product surface layer portion is α transformed by cooling and that the transverse waves of electromagnetic ultrasonic waves are used. In the method described in JP-A-53-106085, in the case where the cooling rate is high and the cooling time is short at the time when the product is cooled, even if the temperature of product is decreased to a value not higher than the Curie point, a non-magnetic γ phase remains, and the magnetism does not recover instantly. On the other hand, in the first method, since the product is cooled until the surface layer portion is α transformed so that the magnetism recovers surely, as an electromagnetic ultrasonic wave generating mechanism, in addition to the effect of Lorentz's force, the effect of magnetostriction is dominant, and thus a high S/N can be obtained. Specifically, as shown in FIG. 1, at a temperature higher than the Curie point, electromagnetic ultrasonic waves are generated by only the effect of Lorentz's force. However, if the steel is cooled, the magnetism recovers and the effect of magnetostriction is added due to supercooling at a temperature slightly lower than the Curie point. Although the effect of Lorentz's force is increased by cooling, the effect of magnetostriction is far greater than the effect of Lorentz's force, so that the sensitivity of electromagnetic ultrasonic waves is increased, and thus a high S/N can be obtained.

As the product surface layer portion α transformed by cooling, a propagation depth in which the depth from the surface depends on the frequency of electromagnetic ultrasonic waves is preferable. For example, when the frequency is 1 MHz, a portion to a depth greater than about 0.1 to 0.2 mm has only to be α transformed. Although it is preferable that the whole structure be made α phase completely by transformation, since the way of α transformation in the surface layer portion is changed by the cooling condition and composition etc. of steel, even if the γ phase remains partially, the effect of the first method can be obtained.

(2) Second Method

A second method is one in which the transverse waves of burst-like electromagnetic ultrasonic waves having the maximum pulse width in which the time of flight is not exceeded, that is, the transverse waves of burst-like electromagnetic ultrasonic waves in which at least one selected from frequency, amplitude, and phase is modulated within a predetermined pulse width set near the maximum time width determined from product thickness, product temperature, and sound velocity are transmitted by a transmitting sensor, the signal after the transmitting signal propagates in the product is received as a receiving signal by a receiving sensor, and correlation operation of receiving signal is performed by using a reference signal of a waveform that is the same as or similar to the transmitting signal.

In the second method, like the method described in JP-A-2000-266730, the correlation operation of receiving signal is performed by using a modulated transmitting signal. The second method is characterized in that the pulse width of transmitting signal is set near the maximum time width determined from product thickness, product temperature, and sound velocity.

Figure 2:
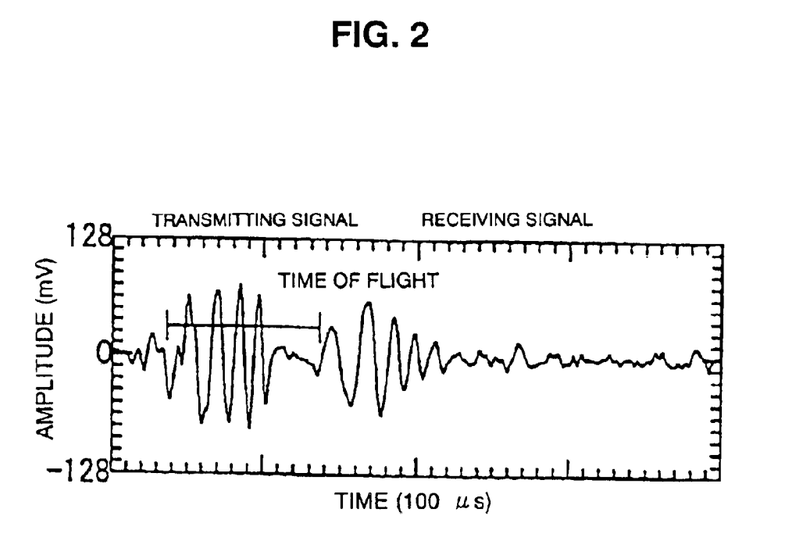
FIG. 2 is a diagram showing the relationship between transmitting signal and time of flight.

As shown in FIG. 2, the receiving signal having propagated in the product appears at a position lagging behind the transmitting signal by time of flight. The time of flight dT can be estimated from the following equation (1) by using product thickness d, product temperature T(x), sound velocity C(T), and average product temperature Ta.

$$dT = \int_0^d dx / C(T(x)) \approx d / C(Ta) \tag{1}$$

Therefore, if the product thickness d and the average product temperature Ta according to the operation conditions are determined beforehand, the time of flight dT can be determined. By setting the maximum pulse width in the range in which this time of flight is not exceeded, the sensitivity of electromagnetic ultrasonic waves is increased, and thus a high S/N can be obtained.

(3) Third Method

A third method is one in which the transverse waves of electromagnetic ultrasonic waves are transmitted repeatedly in pulse units as a transmitting signal by a transmitting sensor, a signal after the transmitting signal propagates in the product is received as a receiving signal by a receiving sensor, the pulses are averaged, and signal processing of receiving signal is performed so that the average number is not less than 16 times and not more than the pulse cycles in which the signal intensity after averaging does not decrease, that is, the change of pulse width caused by the change of signal propagation time is not more than pulse cycles corresponding to measurement time in which the signal intensity is not decreased by pulse addition, preferably 256 times. Specifically, this method is one in which averaging is performed in number of times in which the average number is not less than 16 times and the signal intensity after averaging does not decrease, and the receiving signal is processed in synchronization with the transmitting signal.

Figure 3:
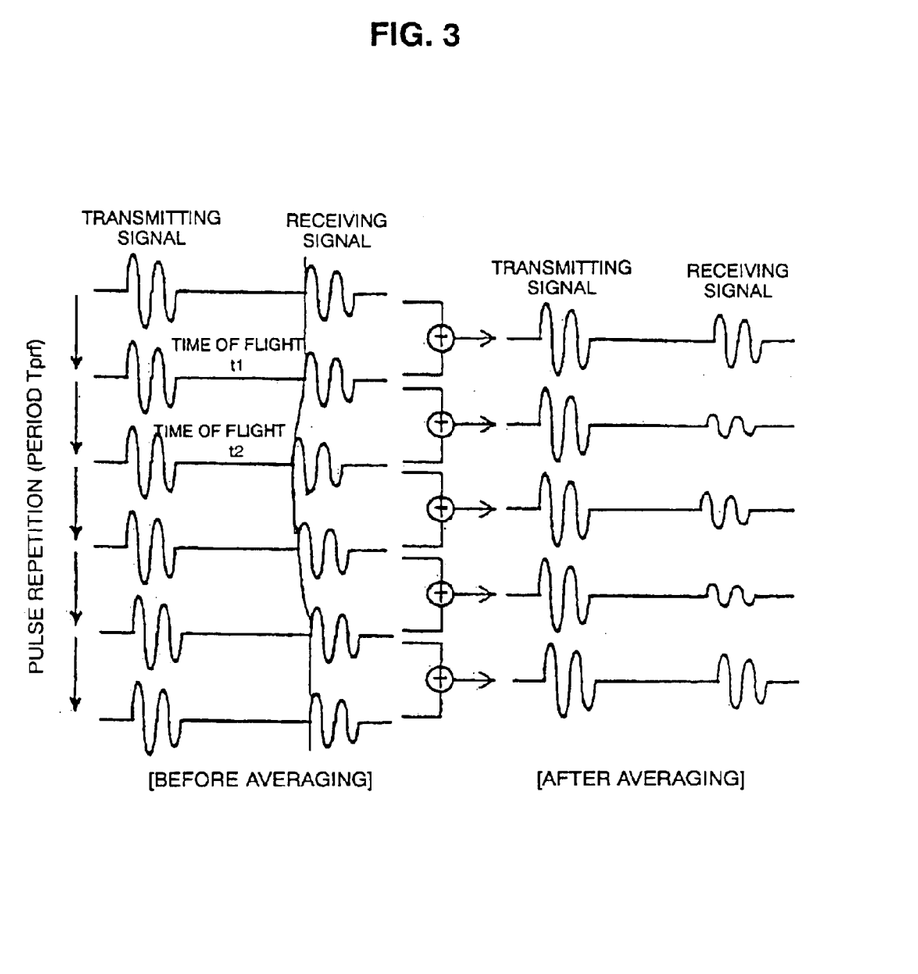
FIG. 3 is a diagram showing the relationship between time of flight and averaging.

If synchronous averaging is performed as in the method described in JP-A-53-57088, since the product temperature changes depending on the operation state, as shown in FIG. 3, the position at which the receiving signal appears changes every moment. Therefore, when the change rate of time of flight is high, the receiving signal after averaging decreases. FIG. 3 shows the case where the average number is two times. If the average number is further increased, the change rate of time of flight further increases, and the receiving signal is further made small.

In the third method, in order to avoid this problem, the average number is determined as described below.

Taking the receiving signal as a sinusoidal wave with a frequency f, the change rate of time of flight per unit time of the receiving signal as τ[=(t2−t1)/T], the pulse repetition frequency as PRF (=1/Tprf), and the average number as Na, the amplitude Xs of receiving signal after averaging is expressed by the following equation (2).

$$x_s = \left| \sum_{i=0}^{Na-1} \sin(2\pi f t + i \cdot \tau / PRF) \right| \tag{2}$$

Also, the amplitude Xn of noise is expressed by the following equation (3)

$$Xn = Na^{-1/2} \tag{3}$$

Therefore, the improvement amount P of S/N after averaging, which can be expressed by the following equation (4), is obtained.

$$P = 20 \log(Xs/Xn) \tag{4}$$

Therefore, the maximum average number is determined based on these equations, and the average number is set so that it does not exceed the maximum number of times, by which a high S/N can be obtained.

If the solidification state of product is judged by the above-described first, second, or third method, by which a high S/N can be obtained, the position of crater end can be detected exactly by a non-contact method. Therefore, if at least one condition selected from the conditions of the casting speed of continuous casting and the quantity of secondary cooling water is controlled based on the detected position of crater end, a high-quality product can be manufactured without a decrease in productivity. For example, if at least one condition selected from the conditions of the casting speed of continuous casting and the quantity of secondary cooling water is controlled based on the detected position of crater end and the crater end is caused to lie in the soft reduction zone, the central segregation at the time of solidification can be decreased, so that a high-quality product can be manufactured.

The improvement in S/N achieved by the above-described first, second, or third method is based on a different principle. Therefore, if these methods are combined, a higher S/N can be obtained.

If by using the above-described first, second, or third method or a method in which these methods are combined, the transverse waves of electromagnetic ultrasonic waves are transmitted and received by using an electromagnet, and the excited current of electromagnet is used as a pulse current continuing for a longer time than the measurement time necessary for solidification judgment, a further higher S/N can be obtained. Therefore, since a sufficient liftoff can be provided, a continuously cast product can be manufactured more stably.

In order to detect the position of crater end from the measurement result of solidification state, as described above, there are two methods: a method for detecting the crater end position by the time of flight of receiving signal and a method for detecting the crater end position from the presence of receiving signal.

In the former method, a phenomenon that the sound velocity of ultrasonic waves depends on the temperature, that is, a phenomenon that the higher the temperature in the product is, the longer the time of flight of ultrasonic waves is utilized. If a set of sensors is surely provided at a position of product on the downstream side of crater end to measure the time of flight of ultrasonic waves, when the crater end comes close to the sensors and the temperature in the product rises, the time of flight becomes long. Therefore, if the relationship between the position of crater end and the time of flight is determined beforehand by a riveting test or by a method in which a plurality of sensors are provided in the casting direction, the position of crater end can be detected.

In the latter method, after the transmitting signal is transmitted, a gate is provided in the time zone in which the receiving signal appears, the maximum value in the gate is determined to determine the intensity of receiving signal, and the presence of receiving signal is judged by checking whether or not the intensity exceeds a certain threshold value, by which the position of crater end is detected. In this method, it is necessary to provide sensors at a plurality of positions along the casting direction of product.

In either of these detecting methods, a receiving signal with a high S/N is obtained by the above-described first, second, or third method or a solidification state measuring method in which these methods are combined, and therefore the time of flight can also be measured with high accuracy, so that the position of crater end can be found exactly.

If the measurement of solidification state is made at a plurality of positions along the widthwise direction of product by the above-described first, second, or third method or a method in which these method are combined, a widthwise profile of crater end is found. If the quantity of secondary cooling water in the widthwise direction is controlled based on the profile, the uniformity of widthwise profile can be achieved, by which a high-quality product with less segregation can be obtained. The measurement at a plurality of positions along the widthwise direction can be made by scanning a set of sensors in the widthwise direction or by providing a plurality of sets of sensors in the widthwise direction.

The position of crater end is detected by the above-described first, second, or third method or a method in which these method are combined, and based on the detected position of crater end, a soft reduction zone for applying soft reduction to the product can be provided, or the product can also be cut.

As a solidification state measuring apparatus for a continuously cast product of steel, which judges the solidification state of product by the above-described first, second, or third method or a method in which these method are combined, the following apparatuses can be applied:

(i) A solidification state measuring apparatus for a continuously cast product of steel having a cooling device for cooling the product until the surface layer portion of product is α transformed, a transmitting electromagnetic ultrasonic wave sensor for transmitting the transverse waves of electromagnetic ultrasonic waves to the cooled product as a transmitting signal, a receiving electromagnetic ultrasonic wave sensor for receiving the signal after the transmitting signal penetrates the product as a receiving signal, and an evaluating section for judging the solidification state of product based on the receiving signal.

(ii) A solidification state measuring apparatus for a continuously cast product of steel having a transmitting electromagnetic ultrasonic wave sensor for transmitting the transverse waves of burst-like electromagnetic ultrasonic waves, in which at least one selected from frequency, amplitude, and phase is modulated within a pulse width that has a magnitude of 50 to 150% of the maximum time width not exceeding the time of flight for propagating in the product, to the product as a transmitting signal, a receiving electromagnetic ultrasonic wave sensor for receiving the signal after the transmitting signal propagates in the product as a receiving signal, a correlation processing section for performing correlation operation of receiving signal by using a reference signal of a waveform that is the same as or similar to the transmitting signal, and an evaluating section for judging the solidification state of product based on the operation result.

(iii) A solidification state measuring apparatus for a continuously cast product of steel having a transmitting electromagnetic ultrasonic wave sensor for transmitting the transverse waves of electromagnetic ultrasonic waves repeatedly in pulse units as a transmitting signal, a receiving electromagnetic ultrasonic wave sensor for receiving the signal after the transmitting signal propagates in the product as a receiving signal, a synchronous averaging section for averaging the pulses and performing signal processing of receiving signal so that the average number is not less than 16 times and not more than the pulse cycles in which the signal intensity after averaging does not decrease, and an evaluating section for judging the solidification state of product based on the result of signal processing.

If the above-described solidification state measuring apparatuses of items (i) to (iii) are combined, a higher S/N can be obtained.

Embodiment 1

Figure 4:
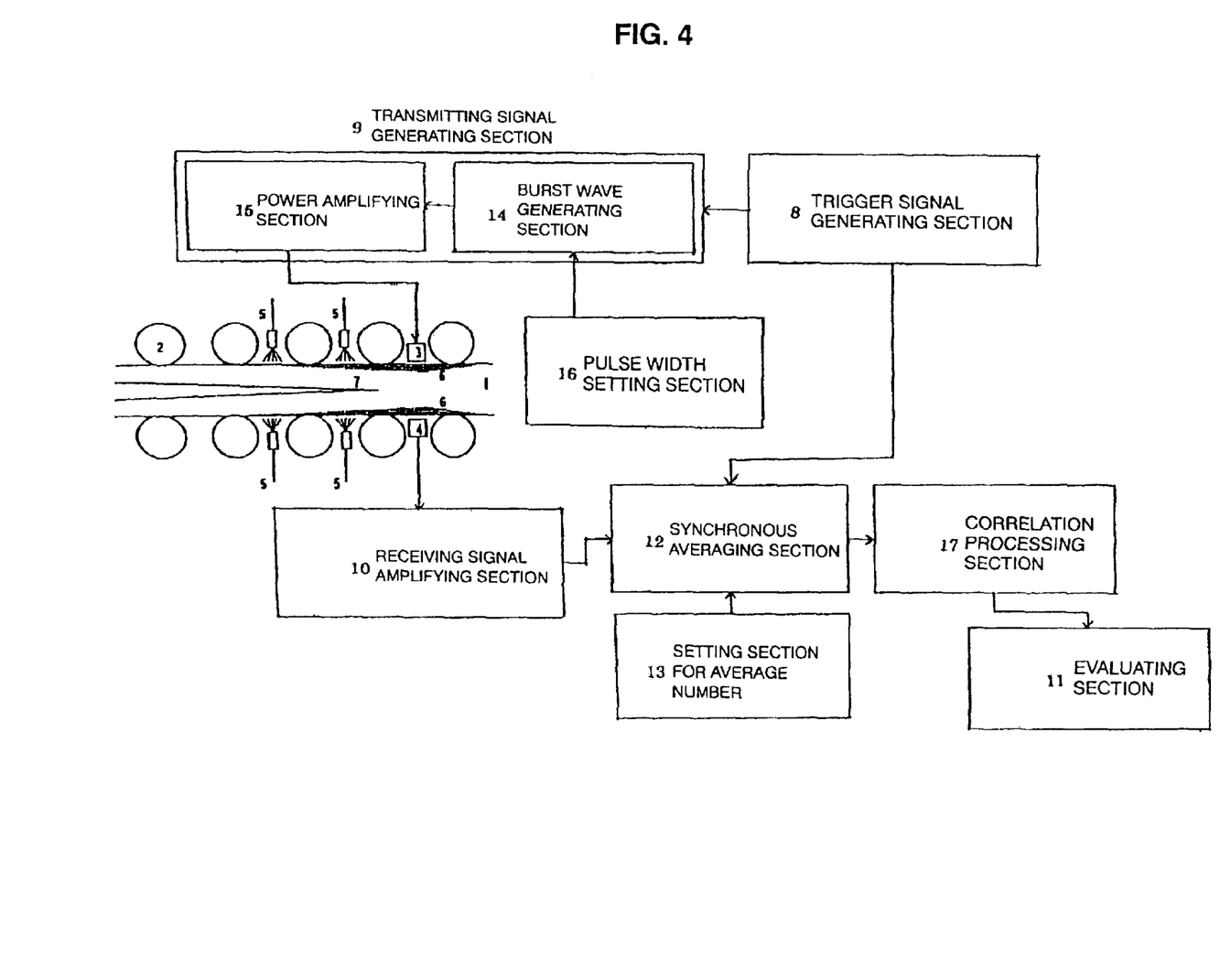
FIG. 4 is a diagram showing one example of a method for measuring the solidification state of product, which is an essential requirement of a method in accordance with the present invention.

FIG. 4 shows one example of a method for measuring the solidification state of product, which is an essential requirement of a method in accordance with the present invention.

A continuously cast product 1 of carbon steel moves to the right side in the figure by support rolls 2. An unsolidified portion 7 exists within the product 1, and the tip end thereof is a crater end. A surface layer portion 6 of the product 1 is cooled by water cooling nozzles 5 provided between the rolls 2, and is transformed from γ phase to α phase. A transmitting electromagnetic ultrasonic wave sensor 3 and a receiving electromagnetic ultrasonic wave sensor 4 are arranged face to face so as to hold the α transformed portion therebetween.

A transmitting output system for outputting the transverse waves of electromagnetic ultrasonic waves from the transmitting electromagnetic ultrasonic wave sensor 3 as a transmitting signal is composed of a trigger signal generating section 8 for transmitting signal, a transmitting signal generating section 9, and a pulse width setting section 16 for setting the pulse width of burst waves. Further, the transmitting signal generating section 9 is composed of a burst wave generating section 14 for generating burst waves of a pulse width set based on the trigger signal and a power amplifying section 15 for amplifying the generated burst waves and outputting them to the transmitting electromagnetic ultrasonic wave sensor 3 as a transmitting signal.

A receiving processing system for receiving the signal after propagating in the product by means of the receiving electromagnetic ultrasonic wave sensor 4 and processing the signal is composed of a receiving signal amplifying section 10, a synchronous averaging section 12, a setting section for average number 13, a correlation processing section 17, and an evaluating section 11 for judging the solidification state from the receiving signal.

When a transmitting timing signal is generated from the trigger signal generating section 8, the burst wave generating section 14 generates a burst-like transmitting signal in which at least one selected from frequency, amplitude, and phase is modulated. Herein, a pulse width is specified by the pulse width setting section 16. The transmitting signal is amplified by the power amplifying section 15, and is applied to the transmitting electromagnetic ultrasonic-wave sensor 3.

Figure 5:
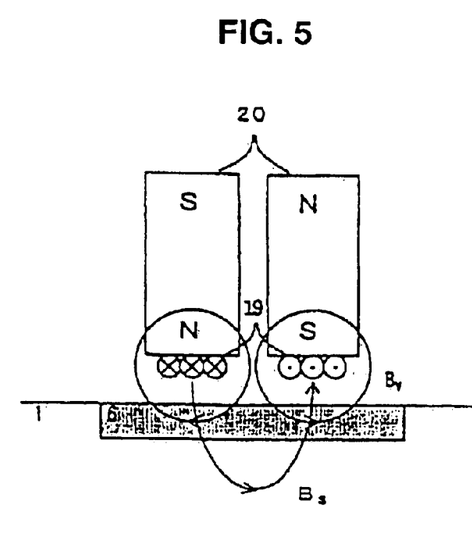
FIG. 5 is a view showing one example of an electromagnetic ultrasonic wave sensor.

As shown in FIG. 5, in the α transformed surface layer portion 6 of the product 1, a high-frequency oscillating magnetic field By caused by the transmitting signal is applied in parallel to the surface of the product 1 by a coil 19 provided in the transmitting electromagnetic ultrasonic wave sensor 3. As a result, since a stress is applied in parallel to the surface of the product 1 by magnetostriction, shear waves or transverse waves are generated. The transmitting electromagnetic ultrasonic wave sensor 3 is provided with a magnet 20 having magnet poles in the vertical direction to increase the effect of magnetostriction by the static magnetic field Bs. This magnet may be a permanent magnet or an electromagnet.

On the opposite surface of the product 1, the receiving electromagnetic ultrasonic wave sensor 4 constructed as shown in FIG. 5 is arranged face to face, and a static magnet field Bs is applied to the α transformed surface layer portion 6 of the product 1 by a magnet. When the transverse waves of electromagnetic ultrasonic waves propagate in the product and reach this portion, the magnetic permeability of this portion is changed by the reverse effect of magnetostriction. As a result, the magnetic flux Bs crossing a coil of the receiving electromagnetic ultrasonic wave sensor 4 changes, so that a voltage is generated in the coil by electromagnetic induction, by which the receiving signal can be obtained.

This receiving signal is amplified by the amplifying section 10, and then is sent to the synchronous averaging section 12, where the receiving signal is averaged by the number of times set by the setting portion for average number 13. In the synchronous averaging section 12, although averaging can be performed by various methods, in this embodiment, the signal is expressed by numbers by performing A/D conversion, and is averaged by a computer in synchronization with the signal of the trigger generating section 8. The averaging can be performed by using the following equation (5).

$$y_i(j) = (1/Na) \cdot \sum_{k=0}^{Na-1} x_{i-k}(j) \tag{5}$$

where, Xi(j) is input signal, Yi(j) is output signal, Na is the average number, i is pulse repetition, and $-\infty \leq i \leq \infty$, $0 \leq j \leq n-1$ (n: number of data for one flaw detection signal).

The averaged receiving signal is sent to the correlation processing section 17, where the signal is subjected to correlation operation by the following equation (6). If the calculation is not performed by using the equation (6), but input signal subjected to FFT (fast Fourier transform) and conjugate of reference signal subjected to FFT are multiplied together, and the result is subjected to inverse FFT and is outputted, processing can be performed at the highest speed.

$$y_i(j) = \sum_{k=0}^{N_c-1} c(k) \cdot x_i(j+k) \tag{6}$$

where, Xi(j) is input signal, Yi(j) is output signal, C(j) is reference signal, Nc is the number of reference signals, i is pulse repetition, and $-\infty \leq i \leq \infty$, $0 \leq j \leq n-1$ (n: number of data for one flaw detection signal).

The burst wave generating section 14 generates the burst-like transmitting signal in which at least one selected from frequency, amplitude, and phase is modulated. As one example of modulation system, frequency modulated chirp waves are shown by the following equation (7).

$$St(t) = \sin[2\pi \cdot (fc - Bw/2 + Bw \cdot t/2Tw) \cdot t] \tag{7}$$

where, fc is central frequency of chirp waves, Bw is a frequency sweep width of chirp waves, Tw is pulse width of chirp waves, and $0 \leq t \leq Tw$.

Since the waveform of receiving signal having propagated in the product 1 is analogous to that of the transmitting signal, the receiving signal having passed through the correlation processing section 17 is caused to have a sharp waveform with a short pulse width by the pulse compression effect that the pulse width of receiving signal is made shorter than that of transmitting signal. This is useful in the following two respects when the solidification state is judged by using the evaluating section 11 successively. The first respect: when the intensity of receiving signal is determined, a gate has only to be provided in the time zone of receiving signal to determine the maximum value in the gate. In the case of a sharp waveform with a short pulse width, excess noise is not picked up. The second respect: when the time of flight of receiving signal is determined, a pulse with a short width increases the time accuracy, so that the solidification state can be judged with high accuracy.

Thus, the solidification state at a measurement position of the product 1 is measured by obtaining the output from the correlation processing section 17 and then judging the solidification state in the evaluating section 11.

The processing in the synchronous averaging section 12, the correlation processing section 17, and the evaluating section 11 can be performed by using one or more computers. Also, in the processing in the evaluating section 11, the presence of receiving signal can be detected by the use of a comparator or by manual means.

Improvement examples of S/N will be described below.

1. In the case where the above-described first method is used

Figure 6:
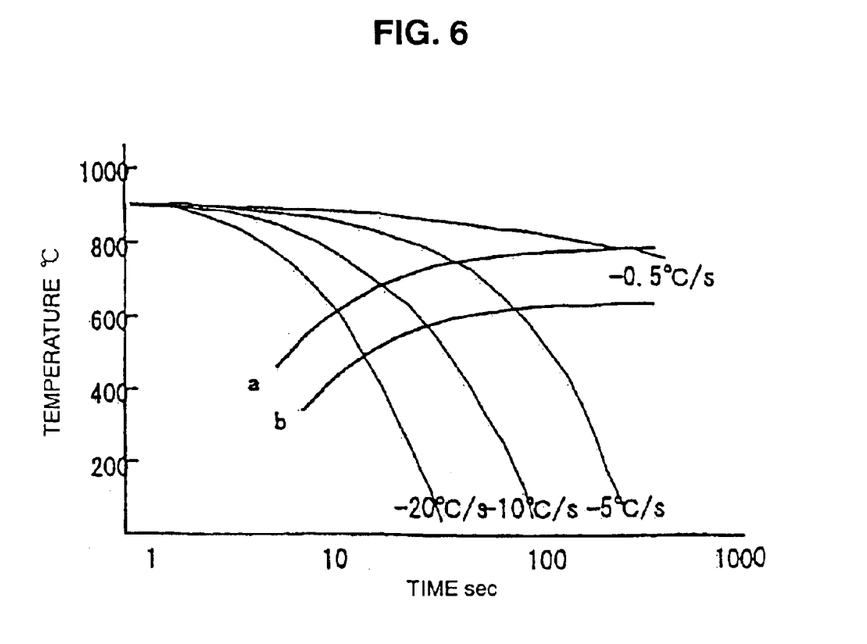
FIG. 6 is a transformation diagram for continuous cooling of steel subjected to a test.

A product having a transformation diagram for continuous cooling shown in FIG. 6, which moves at a speed of 40 mm/s and has a surface temperature of 900° C., was cooled at a cooling rate of −20° C./s by the water cooling nozzles 5 disposed in front of the transmitting electromagnetic ultrasonic wave sensor 3, and the S/N of receiving signal was measured. As seen from FIG. 6, the transformation start temperature (curve a) at the time when the product is cooled at a cooling rate of −20° C./s is about 620° C. The effect of magnetostriction as described by using FIG. 1 increases as the product is cooled to a temperature lower than the transformation end temperature (curve b). In this example, the product was cooled so that the surface temperature thereof is 600° C. to prevent surface cracking etc. Therefore, since a temperature decrease of 300° C. is needed, the length of a cooling zone was set to 300/20×40=600 mm.

As a result, the S/N was improved by 10 dB as compared with the case where such cooling is not performed.

2. In the case where the above-described second method is used

As described above, the receiving signal is received a time of flight late after transmitting, so that the pulse width of transmitting signal must be shorter than the time of flight to prevent the leak of transmitting signal from overlapping with the receiving signal. Also, the time of flight is determined from product thickness, product temperature, and sound velocity, and the sound velocity depends on product temperature T and steel type, being approximately 3000−0.65×T m/s in the case of transverse waves and carbon steel. Therefore, with decreasing temperature, the sound velocity is high, and the time of flight is short.

Thereupon, at a measurement position, since the time of flight is the shortest when the product temperature is the lowest, the time of flight at this time is the maximum time width. Therefore, the pulse width of transmitting signal should be set to a vicinity of this value. In the present invention, since the solidification state of product must be judged, the case where the product temperature is the lowest is thought to be the case where the center temperature of product is about 1100° C. and the average temperature thereof is about 1000° C.

Since the S/N is approximately proportional to the square root of pulse width, if the pulse width is decreased to about ½, the S/N decreases by about 6 dB and the effect becomes little. On the other hand, if the pulse width is too long, overlapping with the receiving signal occurs. At both ends of waveform, the amplitude is somewhat decreased according to the characteristics of sensor and amplifier, so that a pulse width up to 1.5 times of the maximum time width is allowable. Therefore, the range of pulse width in which the S/N can be improved is 50 to 150% of the maximum time width, preferably 80 to 120% thereof.

Table 1 gives the optimal pulse width of transmitting signal determined for products having a thickness of 200 mm, 250 mm, and 300 mm. Herein, the lowest average temperature was set at 1000° C., and the sound velocity at that time was set at 2350 m/s.

TABLE 1

| Product thickness | 200 mm | 250 mm | 300 mm |
|---|---|---|---|
| Min. time of flight | 85 µs | 106 µs | 128 µs |
| Pulse width | 68–102 µs | 85–128 µs | 102–153 µs |

When the leakage signal of transmitting signal is large, a receiving amplifier is saturated by the leakage signal, so that a time dead zone is sometimes produced by a so-called run-in phenomenon. Therefore, when there is a run-in phenomenon, the pulse width has only to be set at a value obtained by subtracting run-in time from the value given in Table 1.

The S/N of receiving signal was actually measured in the case where the thickness is 250 mm, the pulse width is 100 µm, and the frequency is 100 kHz. As a result, the S/N increased by 12 dB as compared with one sinusoidal wave of 100 kHz. Therefore, by setting the pulse width in the aforementioned range, the S/N increases by at least 6 dB.

3. In the case where the above-described third method is used

As described above, as the change rate of time of flight due to temperature change during casting increases, the receiving signal may be made small by averaging. According to the study on the change rate of time of flight, the maximum change rate was about 0.03 to 0.3 µs s/s. Therefore, taking this value as a parameter, and taking the frequency of ultrasonic waves as 100 kHz, and the pulse repetition frequency as 100 Hz, the relationship between average number and amplitude of receiving signal was determined based on the equation (2).

Figure 7:
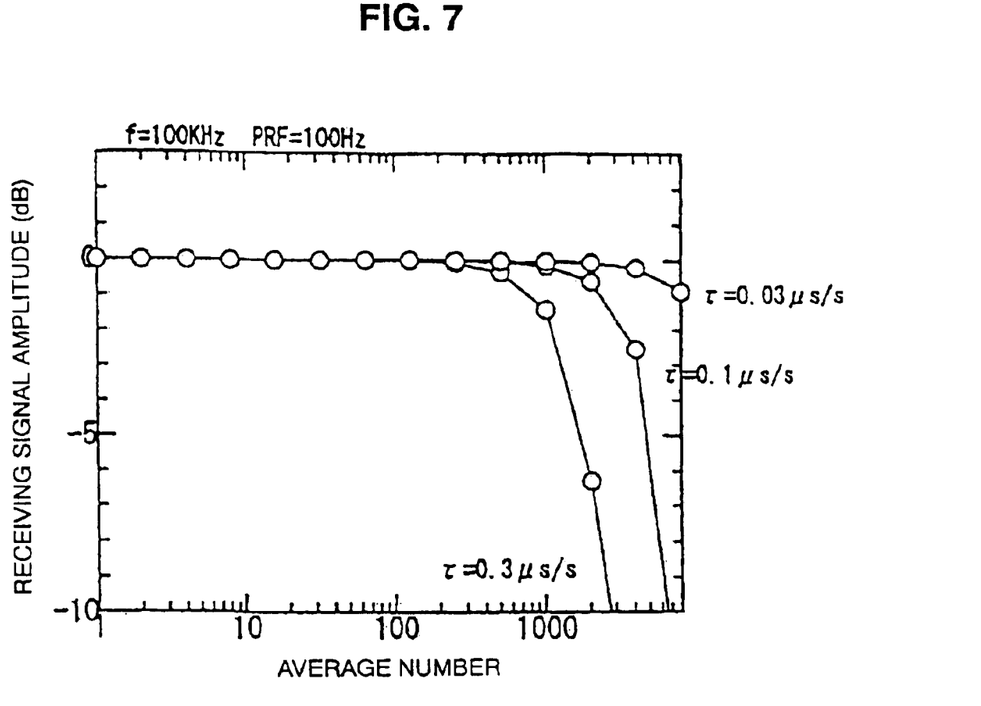
FIG. 7 is a diagram showing the relationship between average number and receiving signal amplitude.

As a result, as shown in FIG. 7, when the change rate τ of time of flight per unit time is the highest of 0.3 µs/s, a decrease in amplitude scarcely occurs if the average number is less than 256 times. Therefore, 256 was specified to be the maximum average number.

At this time, the improvement amount P of S/N shown in the equation (4) is 24 dB. In calculating the maximum average number, a prior condition is that if the decrease in receiving signal intensity is about 1 dB, the amplitude scarcely decreases. Specifically, the maximum average number when the change rate τ of time of flight is 0.3 µs/s is 256 times and the decrease in receiving signal intensity is 1 dB. Even in the case of other change rates τ of time of flight, the maximum average number is calculated in the same way.

Since the less the average number is, the smaller the improvement amount of S/N is, 16 times or more is preferable. In this case, an improvement amount of +12 dB can be obtained. Inversely, if the average number is too large, the amplitude decreases as shown in FIG. 3, so that it is preferable that the average number be within about two times of the above-described maximum average number. The optimal average number is 50 to 200% of the maximum average number.

As is apparent from the equation (2), in the case where the frequency of ultrasonic waves or the pulse repetition frequency is changed, if τ is changed proportionally in FIG. 7, the relationship between average number and amplitude of receiving signal can be determined.

4. In the case where the first, second, and third methods are combined

Since the first, second, and third methods are based on different principles as described above, a combination of all of these methods increases the S/N by 10+6+12=28 dB. Also, since the liftoff sensitivity characteristic of electromagnetic ultrasonic wave sensor is about −4 dB/mm, the liftoff can be widened by 28/4=+7 mm.

Even if all of these methods are not combined, for example, by a method in which the first and second methods are combined, the S/N can be increased by 10+6=16 dB, and the liftoff can be widened by 16/4=+4 mm. Therefore, non-contact measurement can be made surely as compared with the conventional case where the liftoff is 1 to 2 mm.

Similarly, by a method in which the first and third methods are combined, by a method in which the second and third methods are combined, or by the third method in which the average number is 64 times or more, the liftoff can be widened by about +5.5 mm, +4.5 mm, or +4.5 mm, respectively.

Embodiment 2

Figure 8:
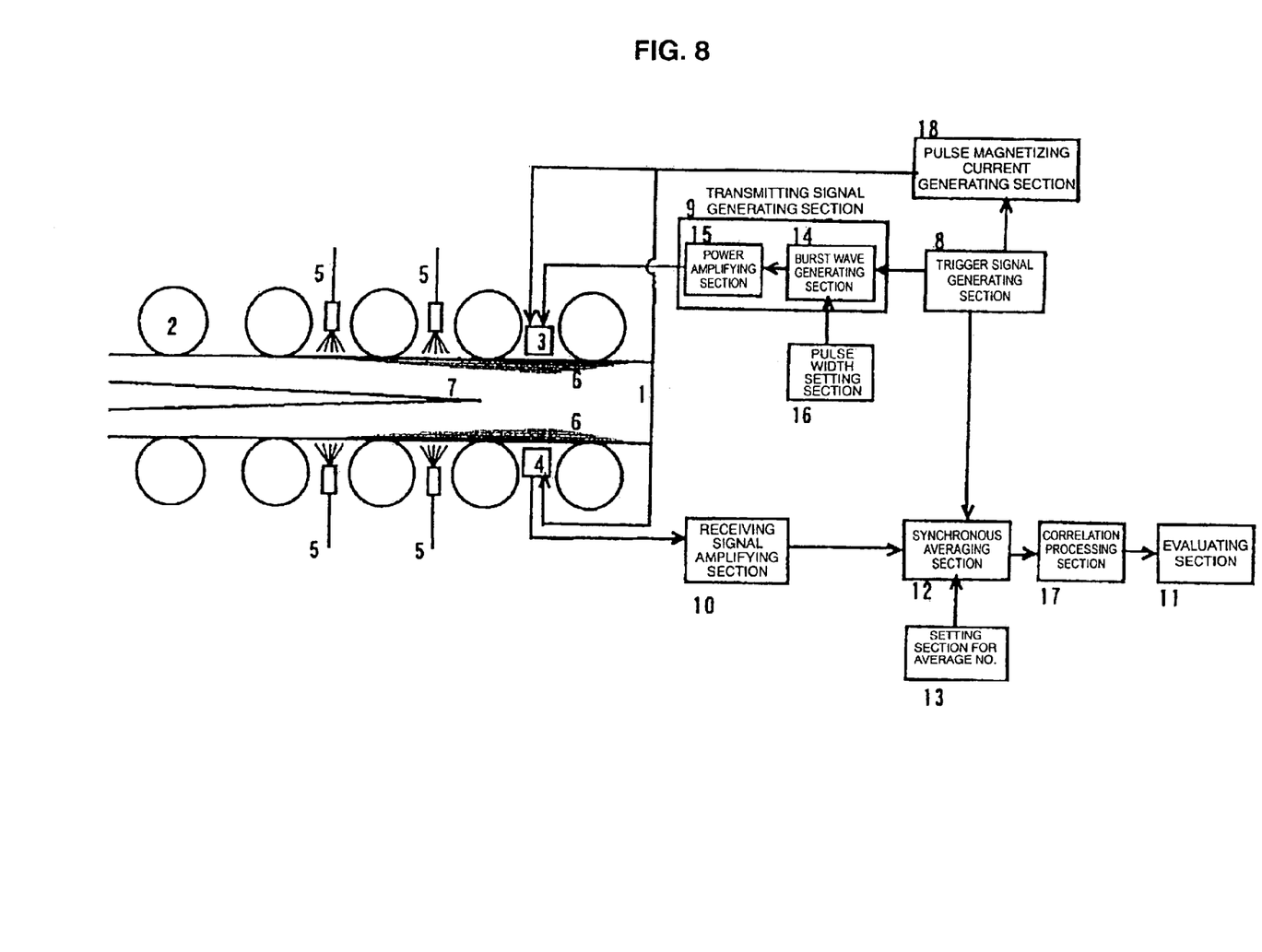
FIG. 8 is a diagram showing another example of a method for measuring the solidification state of product, which is an essential requirement of a method in accordance with the present invention.

FIG. 8 shows another example of a method for measuring the solidification state of product, which is an essential requirement of a method in accordance with the present invention.

In FIG. 8, a pulse magnetizing current generating section 18 for generating a pulse magnetizing current with a high peak-to-peak value to increase a magnetizing force is added to the configuration shown in FIG. 4.

The pulse magnetizing current generating section 18 generates a pulse magnetizing current in synchronization with the signal of the trigger signal generating section 8. The duration of pulse magnetizing current should be a time relating to the ultrasonic wave measurement, and is suitably not shorter than about two times of time of flight, that is, not shorter than 200 $\mu$s. If the duration of pulse magnetizing current is at this level, the time with respect to the repetition frequency of transmitting pulse is about 1/50, so that the calorific value due to magnetizing current is very low, and thus a high current can be carried. Therefore, when a d.c. current was used, the magnetizing current had a limit of about 3 A, but when a pulse magnetizing current was used, a peak-to-peak value of 10 A could be obtained, so that the S/N increased by about 10 dB.

If a pulse magnetizing current is applied to the above-described first, second, or third method, the liftoff can be widened by +5 mm, +4 mm, or +5 mm, respectively.

Even in the case where a d.c. current is used, if the following method (1) or (2) is used, the magnetizing current can be increased to about 10 A, and thus the same effect as that in the case where a pulse magnetizing current is used can be achieved.

(1): The resistance of copper wire is reduced by increasing the diameter of copper wire used for an electromagnet.

(2): The cooling capacity is increased by speeding up the circulation of a cooling medium used for cooling an electromagnet.

Embodiment 3

Figure 9:
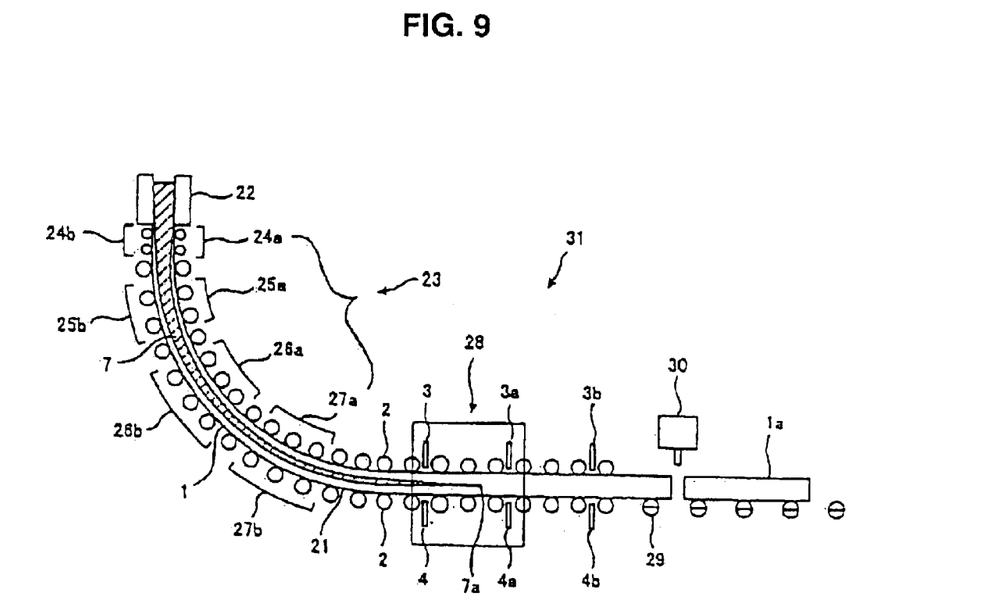
FIG. 9 is a view showing one example of an embodiment of a method in accordance with the present invention.

FIG. 9 shows one example of an embodiment of a method in accordance with the present invention.

A continuous casting machine 31 is provided with a mold 22 for pouring and solidifying molten steel, and under the mold 22, a plurality of product support rolls 2 are arranged face to face. On the downstream side of the product support rolls 2, a plurality of conveying rolls 29 and a gas cutter 30 operated in synchronization with the casting speed of a product 1 are provided. For the product support rolls 2, there is provided a secondary cooling zone 23 consisting of first cooling zones 24a, 24b, second cooling zones 25a, 25b, third cooling zones 26a, 26b, and fourth cooling zones 27a, 27b from a position just under the mold 22 toward the downstream side.

In each cooling zone of the secondary cooling zone 23, secondary cooling water is sprayed from a plurality of spray nozzles for air mist spray or for water spray to the surface of the product 1.

Some of the product support rolls 2 are provided so that the distance between the rolls arranged face to face decreases gradually toward the downstream side in the casting direction of the product 1, by which a soft reduction zone 28 capable of providing a reduction force to the product 1 is formed. The roll distance of the product support rolls 2 can be changed during casting by remote control using hydraulic pressure or an electric motor, so that the soft reduction zone 28 can be provided anywhere, for example, in a curved portion. In other words, the soft reduction zone 28 can be moved to any portion in the casting direction according to a crater end 7a of the product 1.

In this soft reduction zone 28, the soft reduction rate of the product 1 is set at 0.6 to 1.5 mm/min. If the soft reduction rate is lower than 0.6 mm/min, an effect of reducing segregation is little, and on the other hand, if the soft reduction rate exceeds 1.5 mm/min, molten steel is squeezed out in the direction opposite to the casting direction, so that negative segregation is produced in a part of product central portion. Also, the total reduction is set at 2 to 6 mm.

Between the product support rolls 2 on the downstream side of the secondary cooling zone 23, transmitting electromagnetic ultrasonic wave sensors 3, 3a and 3b, and receiving electromagnetic ultrasonic wave sensors 4, 4a and 4b are provided at three points in the casting direction to detect the position of the crater end 7a of the product 1.

In the continuous casting machine 31 constructed as described above, the manufacturing method for a continuously cast product of steel in accordance with the present invention is carried out as described below.

Molten steel poured into the mold 22 through an immersion nozzle is formed into the product 1 having a solidified shell 21 cooled by the mold 22 and an inside unsolidified layer 7, and is continuously drawn to the downside while being supported by the product support rolls 2. The product 1 is cooled by the secondary cooling zone 23 during the time when the product 1 passes through the product support rolls 2, so that the thickness of the solidified shell 21 increases, and finally solidification proceeds to the product central portion. The completely solidified end in the casting direction is the crater end 7a.

The solidification state is measured by the above-described various methods for measuring the solidification state of product by using the transmitting and receiving electromagnetic ultrasonic wave sensors 3, 3a, 3b. 4, 4a and 4b, by which the position of the crater end 7a can be detected exactly.

If soft reduction is applied to a product by the following method M1 or M2 based on the detected position of the crater end 7a, the central segregation of the product 1 can be reduced.

(1) Method M1: When a signal sent from the transmitting electromagnetic ultrasonic wave sensor 3 is detected by the receiving electromagnetic ultrasonic wave sensor 4, the casting speed is increased, or the quantity of secondary cooling water is decreased, by which the position of the crater end 7a is moved to the downstream side in the casting direction. On the other hand, when a signal sent from the transmitting electromagnetic ultrasonic wave sensor 3a is not detected by the receiving electromagnetic ultrasonic wave sensor 4a, the casting speed is decreased, or the quantity of secondary cooling water is increased, by which the position of the crater end 7a is moved to the upstream side in the casting direction. Thus, the crater end 7a is caused to lie within a fixed soft reduction zone 28, whereby the product 1 having less central segregation can be obtained.

(2) Method M2: The position of the soft reduction zone 28 is changed by remote control according to the detected position of the crater end 7a so that the crater end 7a lies within the soft reduction zone 28. Thus, most of the crater end 7a of the product 1 including an unsteady region can be caused to lie within the soft reduction zone 28, so that the product 1 having less central segregation can be obtained throughout from casting start to end.

In order to maximize the productivity of the continuous casting machine 31, the crater end 7a must be moved to a position on the downstream side of the continuous casting machine 31. Therefore, when a signal sent from the transmitting electromagnetic ultrasonic wave sensor 3a is detected by the receiving electromagnetic ultrasonic wave sensor 4a, the casting speed is increased, or the quantity of secondary cooling water is decreased, by which the position of the crater end 7a is moved to the downstream side in the casting direction. On the other hand, when a signal sent from the transmitting electromagnetic ultrasonic wave sensor 3b is not detected by the receiving electromagnetic ultrasonic wave sensor 4b, the casting speed is decreased, or the quantity of secondary cooling water is increased, by which the position of the crater end 7a is moved to the upstream side in the casting direction. Thus, the crater end 7a can be moved to the downstream side of the continuous casting machine 31.

When the crater end 7a is detected continuously, if the position of the crater end 7a changes greatly in the casting direction, that location is stored in a computer, and that location is compared with the position to be cut by the gas cutter 30. When that location corresponds to the position to be cut, the product 1 is cut at a position except that location by the gas cutter 30 to obtain a product 1a. By doing this, porosity and laminar voids produced in the central portion of the product 1 do not appear on the cut surface, and are pressed at following hot rolling, so that decrease in yield due to the porosity and laminar voids can be prevented. If the change rate of the position of the crater end 7a in the casting direction is 0.5 m/min or higher, cutting should be performed at a position at least 1 m separated from that location.

As described above, the position of the crater end 7a can be detected by using the time of flight measured by the electromagnetic ultrasonic wave sensor. Therefore, the casting speed and the quantity of secondary cooling water are regulated depending on the time of flight, whereby the crater end 7a can be maintained at a predetermined position, for example, in the soft reduction zone.

What is claimed is:

1. A manufacturing method for a continuously cast product of steel comprising the steps of:
    detecting a position of a crater end of the product by using a method for measuring a solidification state of the continuously cast product by a sensor arranged so as to be in non-contact with said product; and
    controlling at least one condition selected from the conditions of casting speed and quantity of secondary cooling water based on said detected position of the crater end, said method for measuring a solidification state of the continuously cast product comprising the steps of:
    transmitting transverse waves of electromagnetic ultrasonic waves to said product repeatedly in pulse units as a transmitting signal;
    receiving a signal after said transmitting signal propagates in said product as a receiving signal; and
    judging the solidification state of said product by averaging pulses and performing signal processing of the receiving signal so that the average number is not less than 16 times and not more than pulse cycles in which signal intensity after said averaging does not decrease.

2. The manufacturing method for a continuously cast product of steel according to claim 1, further comprising a step of cooling said product until a surface layer portion thereof is α transformed before the step of transmitting transverse waves of electromagnetic ultrasonic waves to said product repeatedly in pulse units as a transmitting signal.

3. The manufacturing method for a continuously cast product of steel according to claim 2, wherein the solidification state of said product is measured at a plurality of positions along the casting direction of said product to detect the position of a crater end.

4. The manufacturing method for a continuously cast product of steel according to claim 2, wherein it least one condition selected from the conditions of the casting speed and the quantity of secondary cooling water is controlled based on the detected position of the crater end so that the crater end lies within a soft reduction zone.

5. The manufacturing method for a continuously cast product of steel according to claim 2, wherein the solidification state of said product is measured at a plurality of positions along the widthwise direction of said product to detect the position of the crater end.

6. The manufacturing method for a continuously cast product of steel according to claim 1, wherein the transmitting and receiving of transverse waves of electromagnetic ultrasonic waves are performed by using an electromagnet, and an exciting current off said electromagnet is made a pulse current continuing for a longer time than a measuring time necessary for the judgment of solidification.

7. The manufacturing method for a continuously cast product of steel according to claim 1, wherein the solidification state of said product is measured at a plurality of positions along the casting direction of said product to detect the position of a crater end.

8. The manufacturing method for a continuously cast product off steel according to claim 1, wherein at least one condition selected from the conditions of the casting speed and the quantity of secondary cooling water is controlled based on the detected position of the crater end so that the crater end lies within a soft reduction zone.

9. The manufacturing method for a continuously cast product of steel according to claim 1, wherein the solidification state of said product is measured at a plurality of positions along the widthwise direction of said product to detect the position of the crater end.

* * * * *